(12) United States Patent
Hecht et al.

(10) Patent No.: US 6,386,866 B1
(45) Date of Patent: May 14, 2002

(54) ULTRASONIC DENTAL INSERT AND HANDPIECE HAVING A LIGHT SOURCE

(75) Inventors: Robert F. Hecht, Baltimore, MD (US); Horacio R. Cabana, Garden City, NY (US); Peter H Werner, Columbia, PA (US)

(73) Assignee: Dentsply Research & Development Corp.

( * ) Notice: Subject to any disclaimer, the term of this patent is extended or adjusted under 35 U.S.C. 154(b) by 0 days.

(21) Appl. No.: 09/709,155

(22) Filed: Nov. 9, 2000

Related U.S. Application Data

(60) Provisional application No. 60/165,341, filed on Nov. 12, 1999.

(51) Int. Cl.[7] ............................. A61C 1/00; A61C 1/07

(52) U.S. Cl. ......................................... 433/29; 433/119

(58) Field of Search ..................... 433/29, 86, 118, 433/119

(56) References Cited

U.S. PATENT DOCUMENTS

| | | | |
|---|---|---|---|
| 3,109,238 A | | 11/1963 | Marks |
| 3,909,670 A | * | 9/1975 | Wakamatsu et al. ........ 315/276 |
| 4,168,447 A | | 9/1979 | Bussiere et al. ............. 310/316 |
| 4,184,196 A | | 1/1980 | Moret et al. ................... 433/29 |
| 4,634,376 A | | 1/1987 | Mossle et al. ................. 433/29 |
| 4,634,379 A | | 1/1987 | Nash .......................... 433/166 |
| 4,642,738 A | | 2/1987 | Meller ........................ 362/119 |
| 4,790,751 A | | 12/1988 | Reinhardt ..................... 433/29 |
| 4,840,563 A | | 6/1989 | Altendorf ...................... 433/29 |
| 5,730,594 A | | 3/1998 | Sharp .......................... 433/119 |
| 5,845,987 A | * | 12/1998 | Painter ....................... 362/206 |
| 6,095,810 A | | 8/2000 | Bianchetti .................... 433/29 |
| 6,268,699 B1 | * | 7/2001 | Woodward et al. ......... 313/634 |

* cited by examiner

Primary Examiner—Cary E. O'Connor
(74) Attorney, Agent, or Firm—Dale R. Lovercheck; James B. Bieber

(57) ABSTRACT

A method of lighting a scaling tip including providing a light source electrically connected to a secondary coil, and providing a scaling tip having an arm extending into a primary coil and adapted to be ultrasonically vibrated by the primary coil.

22 Claims, 7 Drawing Sheets

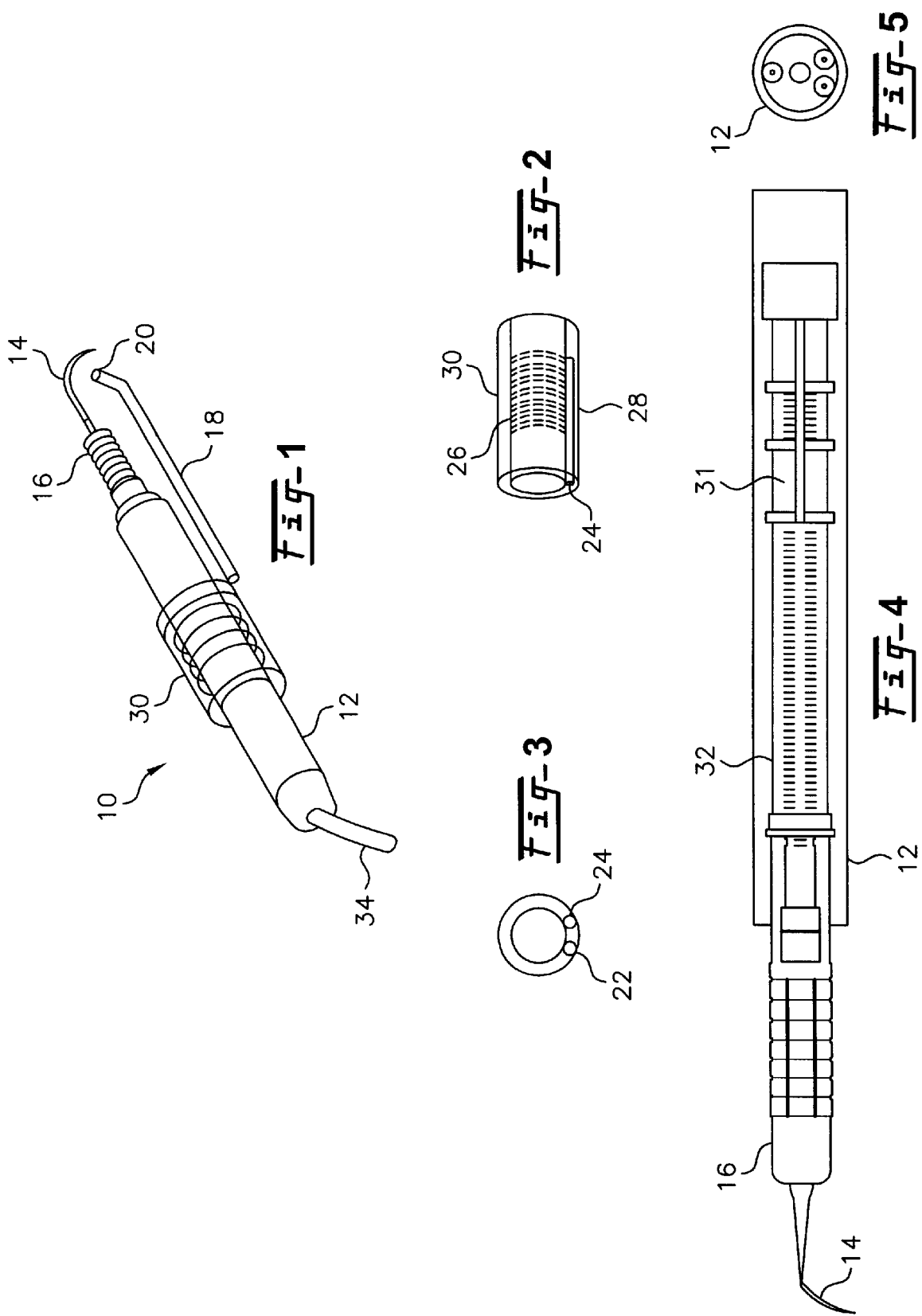

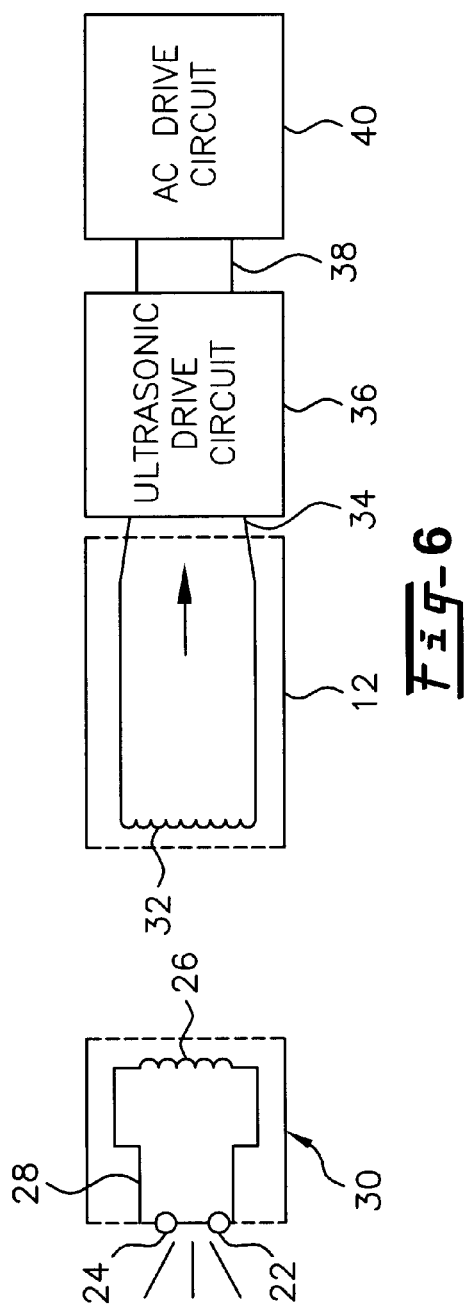
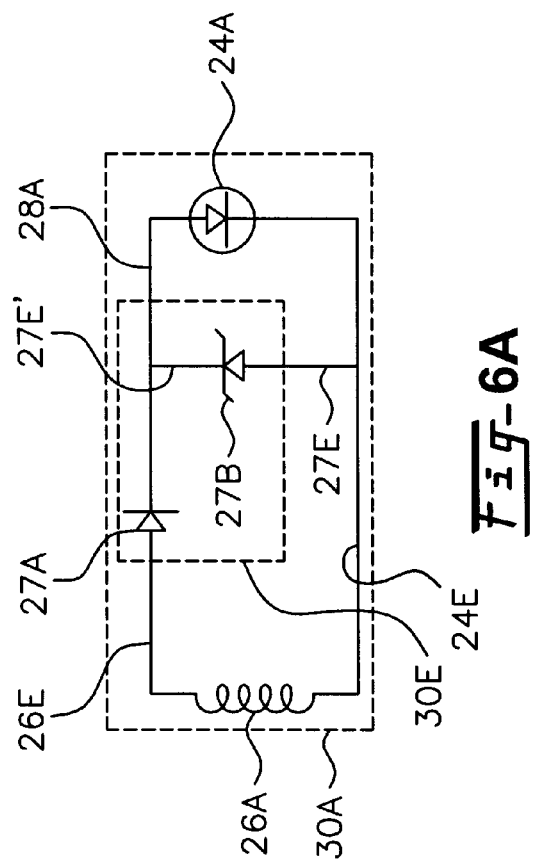
Fig-6
Fig-6A

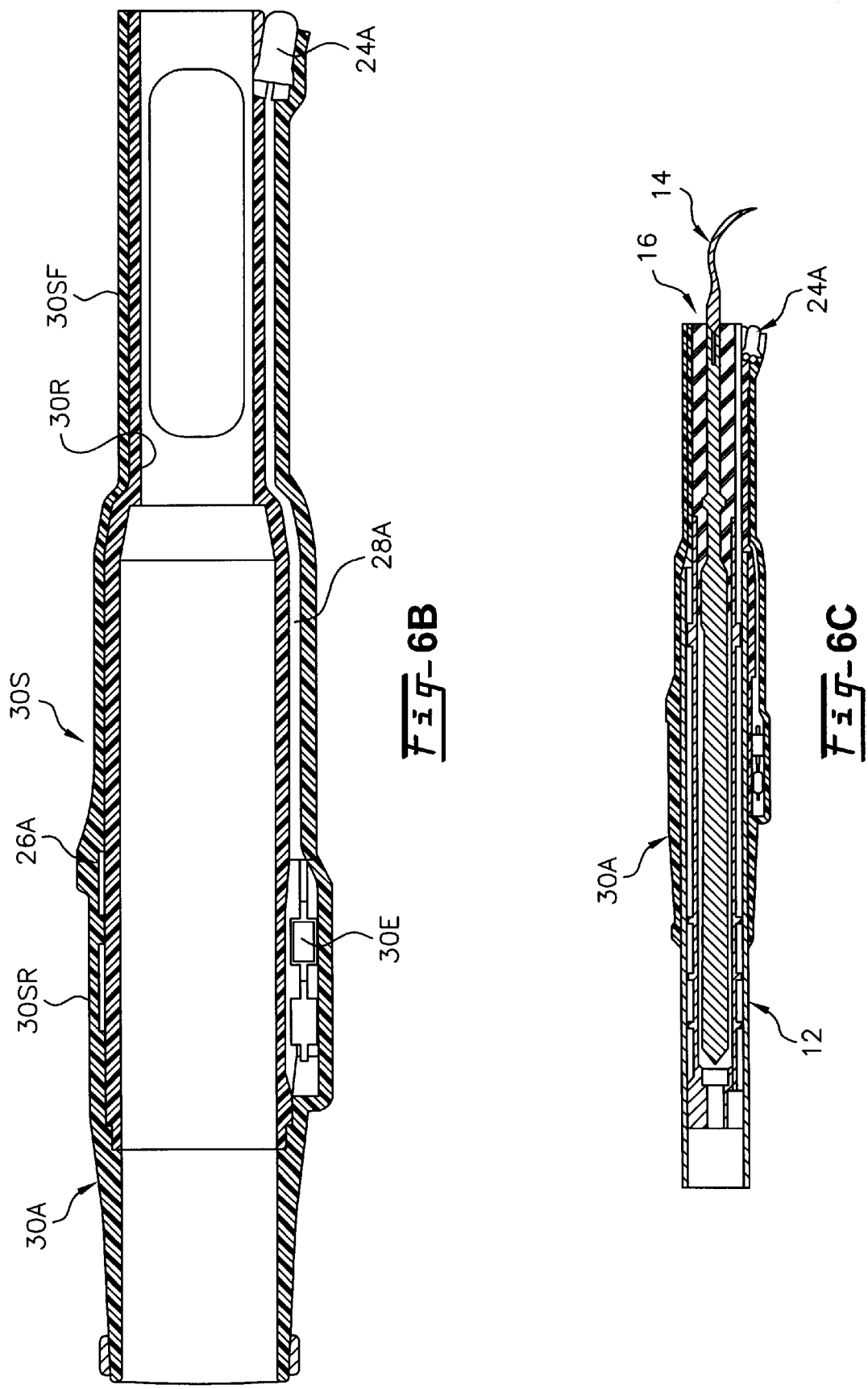

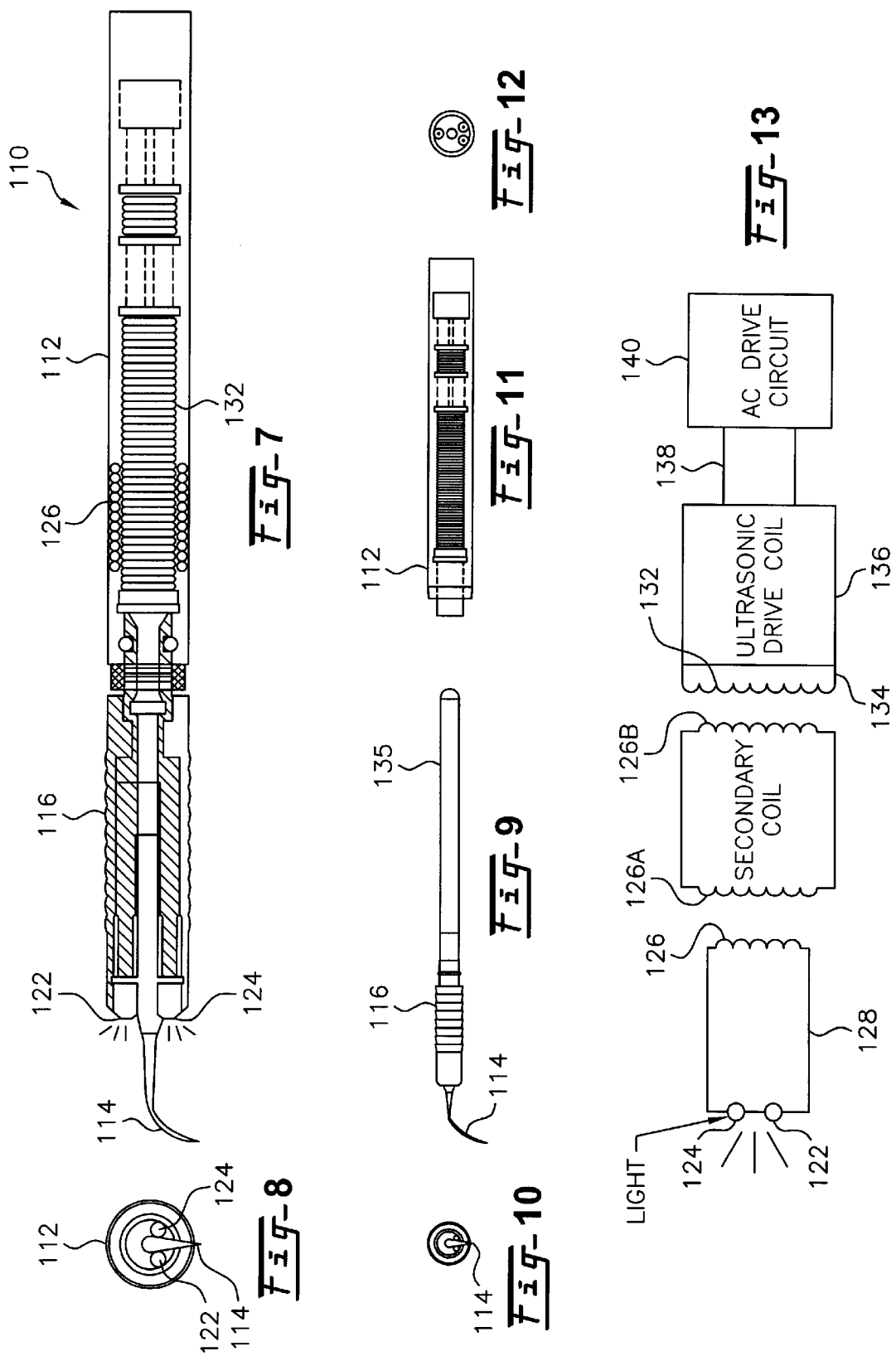

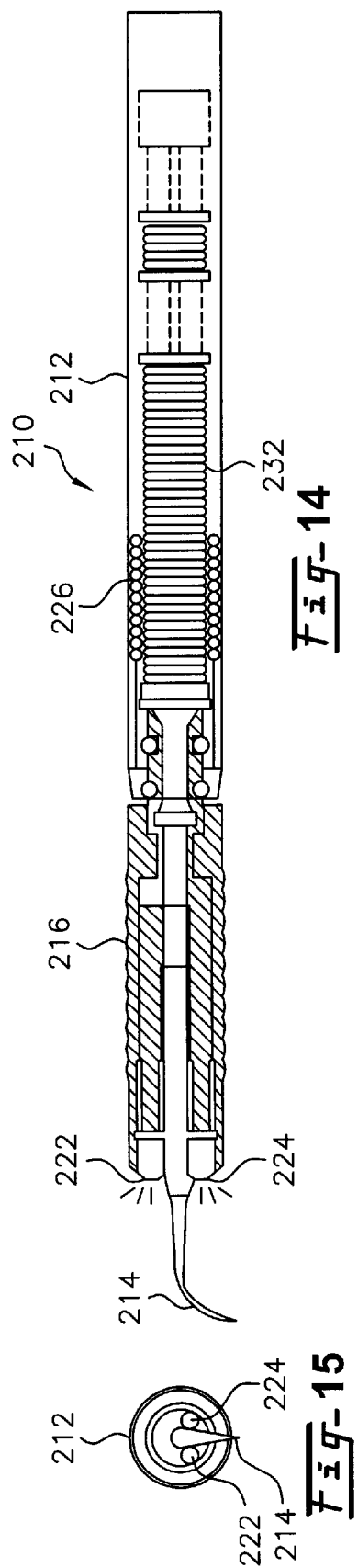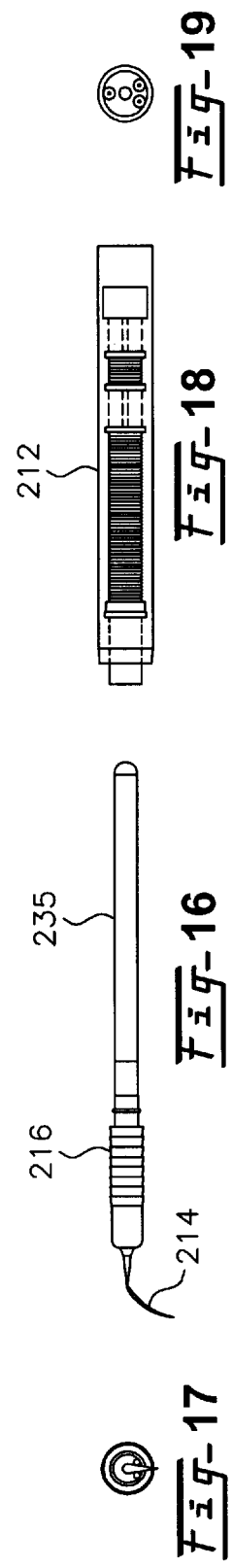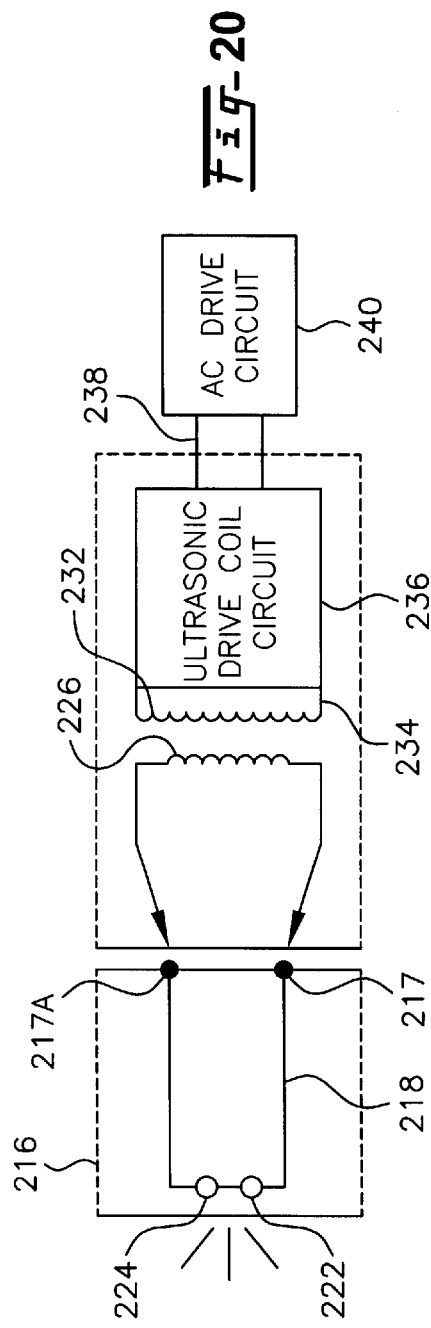

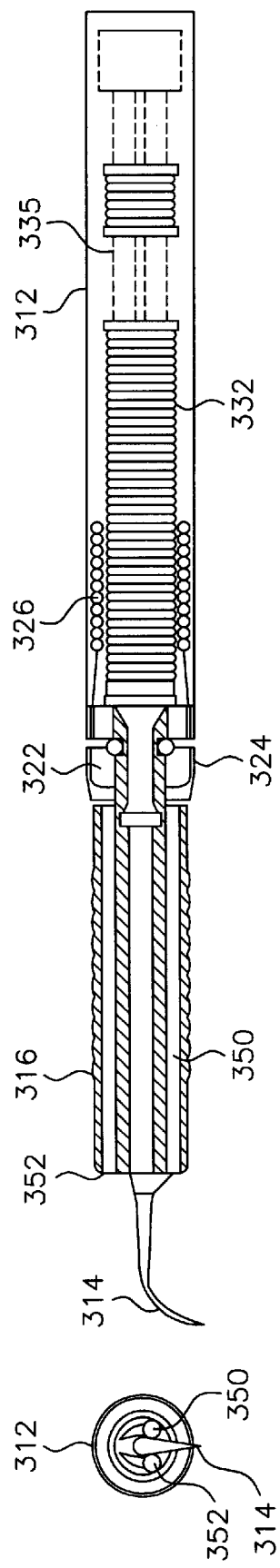
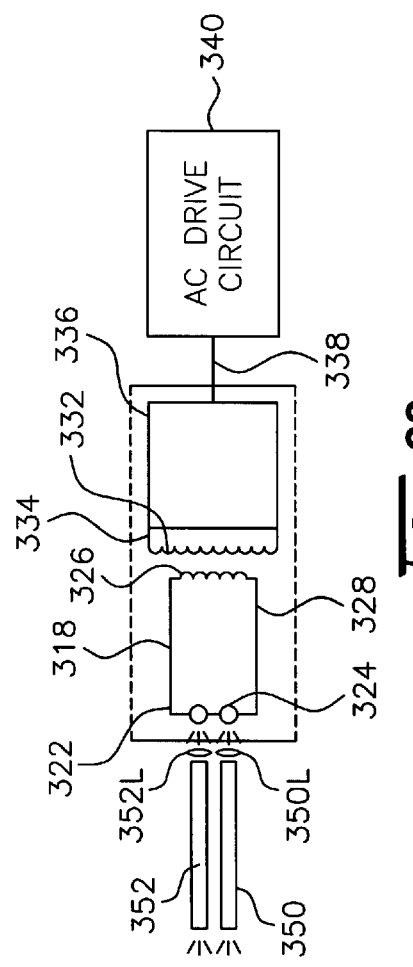

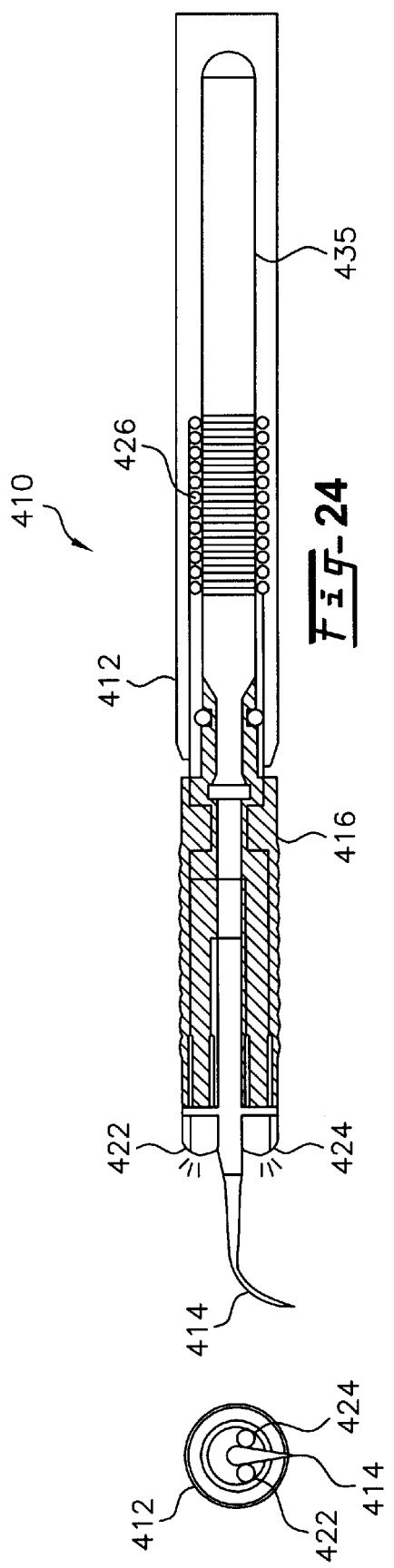
Fig-24
Fig-25
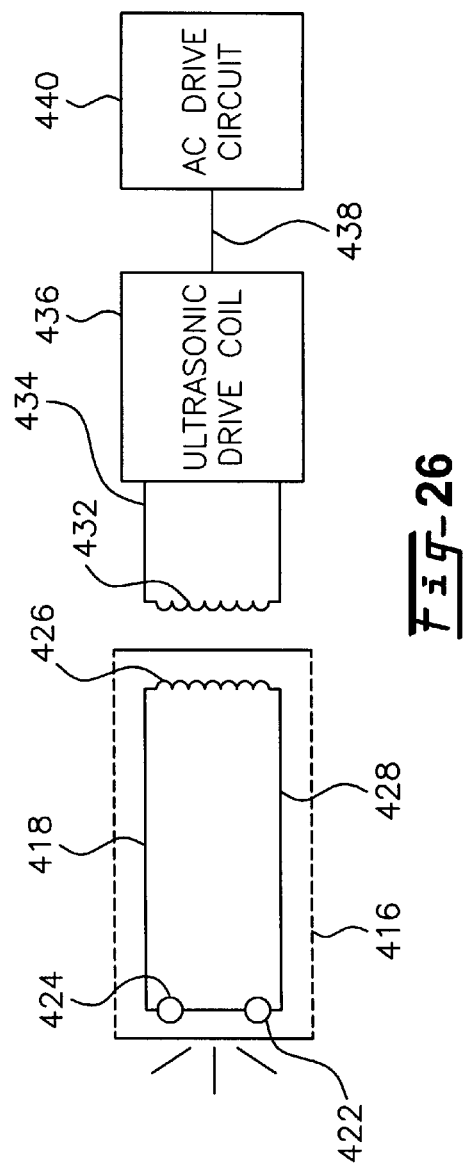
Fig-26

ULTRASONIC DENTAL INSERT AND HANDPIECE HAVING A LIGHT SOURCE

This application claims the benefit of provisional patent application Ser. No. 60/165,341 filed Nov. 12, 1999.

The invention relates to ultrasonic magnetostrictive dental scaler handpieces. The invention provides ultrasonic magnetostrictive dental scaler handpieces having a light source.

Dental handpieces having a light source are disclosed by Bianchetti in U.S. Pat. No. 6,095,810 and Mossle et al in U.S. Pat. No. 4,634,376. The prior art does not disclose a dental method, including: providing a scaling tip having an arm extending into a primary coil enclosed by a housing and sliding a secondary coil over the housing.

The prior art does not disclose an ultrasonic handpiece system comprising a scaling tip, a light guide, at least one light source, a primary coil and a secondary coil, wherein the scaling tip has a metal arm extending into the primary coil and adapted to be ultrasonically vibrated by the primary coil, the secondary coil is positioned to be inductively coupled to the primary coil, the light source is connected by at least one electrical conductor to the secondary coil, the light source is positioned to transmit light into the light guide.

The prior art does not provide an ultrasonic handpiece system, comprising: a scaling tip, at least one light source, a primary coil and a secondary coil, wherein the scaling tip has a metal arm extending into the primary coil and adapted to be ultrasonically vibrated by the primary coil, the secondary coil is supported by the metal arm and positioned to be inductively coupled to the primary coil, and the light source is connected by at least one electrical conductor to the secondary coil, and the light source is positioned to transmit light adjacent to the tip.

The problems of the prior art are overcome by the present invention.

OBJECTS OF THE INVENTION

It is an object of the invention to provide a dental method, comprising: providing a scaling tip having an arm extending into a primary coil enclosed by a housing and sliding a secondary coil over the housing.

It is an object of the invention to provide an ultrasonic handpiece system comprising a scaling tip, a light guide, at least one light source, a primary coil and a secondary coil, wherein the scaling tip has a metal arm extending into the primary coil and adapted to be ultrasonically vibrated by the primary coil, the secondary coil is positioned to be inductively coupled to the primary coil, the light source is connected by at least one electrical conductor to the secondary coil, the light source is positioned to transmit light into the light guide.

It is an object of the invention to provide an ultrasonic handpiece system, comprising: a scaling tip, at least one light source, a primary coil and a secondary coil, wherein the scaling tip has a metal arm extending into the primary coil and adapted to be ultrasonically vibrated by the primary coil, the secondary coil is supported by the metal arm and positioned to be inductively coupled to the primary coil, and the light source is connected by at least one electrical conductor to the secondary coil, the light source is positioned to transmit light adjacent to the tip.

BRIEF DESCRIPTION OF THE DRAWING

FIG. 1 is a perspective view of an ultrasonic handpiece system in accordance with the invention.

FIG. 2 is a partial side view of the ultrasonic handpiece of the system shown in FIGS. 1 through 6.

FIG. 3 is a front view of the ultrasonic handpiece of the system shown in FIGS. 1 through 6.

FIG. 4 is a side view of a detached handpiece of the ultrasonic handpiece system shown in FIGS. 1 through 6.

FIG. 5 is a rear view of a detached handpiece of the ultrasonic handpiece system shown in FIGS. 1 through 6.

FIG. 6 is a schematic electrical circuit diagram of the ultrasonic handpiece system shown in FIGS. 1 through 6.

FIG. 6A is a schematic electrical diagram of the alternative sliding plastic member shown in FIG. 6B.

FIG. 6B is a cross-sectional side view of an alternative sliding plastic member having a single light for use in place of sliding plastic member of the electrical circuit shown in FIG. 6.

FIG. 6C is a cross-sectional side view of the alternative sliding plastic member shown is FIG. 6B positioned on a handpiece.

FIG. 7 is a side view of an ultrasonic handpiece system in accordance with the invention.

FIG. 8 is a front view of the ultrasonic handpiece of the system shown in FIGS. 7 through 13.

FIG. 9 is a side view of the insert of the ultrasonic handpiece of the system shown in FIGS. 7 through 13.

FIG. 10 is a front view of the insert of the ultrasonic handpiece system shown in FIGS. 7 through 13.

FIG. 11 is a side view of a detached handpiece of the ultrasonic handpiece system shown in FIGS. 7 through 13.

FIG. 12 is a rear view of a detached handpiece of the ultrasonic handpiece system shown in FIGS. 7 through 13.

FIG. 13 is a schematic electrical diagram of the ultrasonic handpiece system shown in FIGS. 7 through 13.

FIG. 14 is a side view of an ultrasonic handpiece system in accordance with the invention.

FIG. 15 is a front view of the ultrasonic handpiece of the system shown in FIGS. 14 through 20.

FIG. 16 is a side view of the insert of the ultrasonic handpiece of the system shown in FIGS. 14 through 20.

FIG. 17 is a front view of the insert of the ultrasonic handpiece system shown in FIGS. 14 through 20.

FIG. 18 is a side view of a detached handpiece of the ultrasonic handpiece system shown in FIGS. 14 through 20.

FIG. 19 is a rear view of a detached handpiece of the ultrasonic handpiece system shown in FIGS. 14 through 20.

FIG. 20 is a schematic electrical diagram of the ultrasonic handpiece system shown in FIGS. 14 through 20.

FIG. 21 is a side view of an ultrasonic handpiece system in accordance with the invention.

FIG. 22 is a front view of the ultrasonic handpiece of the system shown in FIGS. 21 through 23.

FIG. 23 is a schematic electrical diagram of the ultrasonic handpiece system shown in FIGS. 21 through 23.

FIG. 24 is a side view of an ultrasonic handpiece system in accordance with the invention.

FIG. 25 is a front view of the ultrasonic handpiece of the system shown in FIGS. 24 through 26.

FIG. 26 is a schematic electrical diagram of the ultrasonic handpiece system shown in FIGS. 24 through 26.

SUMMARY OF THE INVENTION

The invention provides a dental method, comprising: providing a scaling tip having an arm extending into a primary coil enclosed by a housing and sliding a secondary coil over the housing.

The invention provides a lighting device, consisting essentially of: a coil, a control circuit and a light source, the coil being connected to the control circuit and to the light source.

The invention provides an ultrasonic scaler handpiece system, comprising: a scaler handpiece housing supporting a scaling tip, enclosing a primary coil, and a light source housing supporting a secondary coil and a light source, the scaler handpiece housing supporting the light source housing.

The invention provides a method comprising: sliding a lighting sleeve onto a dental handpiece, the dental handpiece enclosing a primary coil, the lighting sleeve, having a secondary coil, and a light source, the secondary coil being connected to the light source.

The invention provides an ultrasonic handpiece system comprising a scaling tip, a light guide, at least one light source, a primary coil and a secondary coil, wherein the scaling tip has a metal arm extending into the primary coil and adapted to be ultrasonically vibrated by the primary coil, the secondary coil is positioned to be inductively coupled to the primary coil, the light source is connected by at least one electrical conductor to the secondary coil, the light source is positioned to transmit light into the light guide.

The invention provides an ultrasonic handpiece system, comprising: a scaling tip, at least one light source, a primary coil and a secondary coil, wherein the scaling tip has a metal arm extending into the primary coil and adapted to be ultrasonically vibrated by the primary coil, the secondary coil is supported by the metal arm and positioned to be inductively coupled to the primary coil, and the light source is connected by at least one electrical conductor to the secondary coil, the light source is positioned to transmit light adjacent to the tip.

DETAILED DESCRIPTION OF THE INVENTION

The invention is now described with more particular reference to FIGS. 1 through 26. With more particular reference to FIGS. 1 through 6 is seen an ultrasonic handpiece system 10, comprising: handpiece housing 12, scaling tip 14, insert 16, light guide 18 having light guide end 20, light sources 22 and 24, a primary coil 32 and a secondary coil 26. Secondary coil 26 is connected to light sources 22 and 24 by electrical conductor 28. Secondary coil 26 is embedded in sliding plastic member 30. Primary coil 32 is connected to ultrasonic drive circuit 36 by electrical conductor 34. Ultrasonic drive circuit 36 by electrical conductor 38 to alternating current drive circuit 40. Alternating current drive circuit 40 is connected to a power source, such as a 110 volt alternating current power source. The scaling tip 14 has a metal arm 31 extending into the primary coil 32 and adapted to be ultrasonically vibrated by the primary coil 32. The secondary coil 26 is supported by the metal arm 31 and positioned to be inductively coupled to the primary coil 32. The light source 22 and 24 are connected by an electrical conductor to the secondary coil 26. The light source 22 is positioned to transmit light adjacent to the tip 14. Preferably, the light from the light source 22 is transmitted onto a tooth positioned adjacent to the tip 14.

The inductively coupled ultrasonic lighted handpiece system 10 provides power to light sources 22 and 24 through inductive coupling for the purpose of illuminating the tip 14 and adjacent tooth. An ultrasonic dental handpiece 10 comprises of a wound wire solenoid, or coil 32, which produces a magnetic field when an electrical current is introduced. This magnetic field provides power for a magnetostrictive motor, which converts electrical power into mechanical motion. The magnetostrictive actuator converts electrical energy to high frequency mechanical energy using the magnetic field induced by an electric current in a wound wire solenoid, or coil 32. The mechanical energy produced is transmitted through a connecting body to the scalar tip 14. This scalar tip motion is used to remove calculus or stains in dental procedures.

With more particular reference to FIGS. 6A, 6B and 6C is seen an alternative sliding plastic member 30A having a single light in light control circuit 30E for use in place of sliding plastic member 30. Sliding plastic member 30 has outer soft polymeric layer 30S and rigid inner polymeric layer 30R. Outer soft polymeric layer 30S is formed in two sections: a front section 30SF and a rear section 30SR. Light control circuit 30E has light emitting diode 24A connected by electrical conductor 28A through diode 27A and an electrical conductor 26E to the secondary coil 26A. Light emitting diode 24A is connected by electrical conductors 28A and 27E' through diode 27B and an electrical conductor 24E to the secondary coil 26A. When sliding plastic member 30A is slid into position for use on handpiece housing 12, light emitting diode 24A is positioned to transmit light adjacent to the tip 14. Preferably during use, the light from the light emitting diode 24A is transmitted onto a tooth positioned adjacent to the tip 14. In FIG. 6C sliding plastic members 30A is shown in operative position slid over handpiece housing 12 having insert 16 with scaling tip 14 inserted within housing 12.

Sliding plastic members 30 and 30A are useful with handpieces which may be operated independently of sliding plastic members 30 and 30A. In accordance with the invention sliding plastic members 30 and 30A may be slide over prior scaler handpiece housings, for example, the housing of handpiece [16 or 316] of the system disclosed in U.S. Pat. No. 6,030,212 or scaler housing [12] of the system disclosed in U.S. patent application Ser. No. 09/467,494 filed Dec. 20, 1999, the disclosures of which are each incorporated herein by reference in their entirety.

Ultrasonic dental handpieces of the invention have an inductively coupled light source. The inductive coupling utilizes an additional coil around the existing coils magnetic field in order to produce the power required to generate light. There are three preferred locations for the inductive coil. The first two include has the inductive coil residing either external to the hand-piece, possibly a separate device, or integrated internally within the existing coil windings in the handpiece. In a magnetostrictive type handpiece the magnetostrictive material is typically attached to the ultrasonic dental insert. For this device, the coil 32 is wound directly around the magnetostrictive material. The available power in these coils would is sufficient to power a light source. The light illuminate the tip and working area. This lighted portion of the ultrasonic handpiece assist the dentist or hygenist in illuminating the dental scaling procedure area. FIG. 1 shows the inductive coupled ultrasonic lighted ultrasonic scalar insert to facilitate in the comprehension of the device. The light source 22 is preferably an incandescent bulb, halogen bulb, or light emitting diode (LED).

The capability of transmitting light eliminates the need for supplemental external light sources during a dental scaling procedure. The light source utilizes the power available in the coil of the handpiece. An additional inductive coil utilize the available power in the coil magnetic field. The device operate in the ultrasonic frequency range, frequencies greater than 18 K Hertz, but it not is specifically limited to this frequency range. The significance of operating in the ultrasonic frequency range is the scaling performance. The higher frequencies are considered optimal for scale removal because it is efficient and provides higher patient comfort in comparison to the relatively lower frequency units.

In a preferred embodiment of the invention a slide over handpiece lighting device is slid over an ultrasonic magnetostrictive dental scaler handpiece, which has an inner coil. The slide over handpiece device preferably includes an external sheath, a coil (an outer coil in relation to the inner coil of the ultrasonic magnetostrictive dental scaler handpiece), which preferably has from 10 to 300 turns, and a light source. In use an induced current flow in the outer coil results from transferred energy by electromagnetic coupling from the inner coil. The induced current flow produces light from the light source.

The light transmitting capability of the handpiece adds illumination to the dental scaling procedure site. This device illuminates the site and allows the ultrasonic insert to rotate in the handpiece allowing easier tip manipulation. The location where light is introduced eliminates the possibility of hand or finger obstructions. Utilizing power from the coil is preferred as this does not require additional wiring in the handpiece or cable which would lends to hand fatigue during scaling. The entire device is autoclave sterilizable.

Insert Light

With more particular reference to FIGS. 7 through 13 is seen an ultrasonic handpiece system 110 comprising: handpiece housing 112, scaling tip 114, insert 116, light sources 122 and 124, a primary coil 132 and secondary coils 126A and 126B, and tertiary coil 126. Tertiary coil 126 is connected to light sources 122 and 124 by electrical conductor 128. Primary coil 132 is connected to ultrasonic drive circuit 136 by electrical conductor 134. Ultrasonic drive circuit 136 by electrical conductor 138 to alternating current drive circuit 140. Alternating current drive circuit 140 is connected to a power source, such as a 110 volt alternating current power source. Scaling tip 114 has a metal arm 135 extending into the center of primary coil 132 and adapted to be ultrasonically vibrated by the primary coil 132. Secondary coils 126A and 126B are supported by the metal arm 135 and positioned to be inductively coupled to the primary coil 132. Light sources 122 and 124 are connected by electrical conductor 128 to tertiary coil 126, and the light sources are positioned to transmit light adjacent to the tip 114.

With more particular reference to FIGS. 14 through 20 is seen an ultrasonic handpiece system 210, comprising; handpiece housing 212, scaling tip 214, insert 216, light sources 222 and 224, a primary coil 232 and a secondary coil 226. Secondary coil 226 is connected to light sources 222 and 224 by electrical conductor 218. Secondary coil 226 is connected through contacts 217 and 217A and electrical conductor 218 to light sources 222 and 224. Primary coil 232 is connected to ultrasonic drive circuit 236 by electrical conductor 234. Ultrasonic drive circuit 236 by electrical conductor 238 to alternating current drive circuit 240. Alternating current drive circuit 240 is connected to a power source, such as a 110 volt alternating current power source. The scaling Up 214 has a metal arm 235 extending into the primary coil 232 and adapted to be ultrasonically vibrated by the primary coil 232. The secondary coil 226 is supported by the metal arm 235 and positioned to be inductively coupled to the primary coil 232. The light source 222 and 224 are connected by an electrical conductor to the secondary coil 226. The light source 222 is positioned to transmit light adjacent to the tip 214.

With more particular reference to FIGS. 21 through 23 is seen an ultrasonic handpiece system 310, comprising: handpiece housing 312, scaling tip 314, insert 316, light sources 322 and 324, light guides 350 and 352, lenses 350L and 352L, a primary coil 332 and a secondary coil 326. Secondary coil 326 is connected to light sources 322 and 324 by electrical conductors 318 and 328. Primary coil 332 is connected to ultrasonic drive circuit 336 by electrical conductor 334. Ultrasonic drive circuit 336 by electrical conductor 338 to alternating current drive circuit 340. Alternating current drive circuit 340 is connected to a power source, such as a 110 volt alternating current power source. The scaling tip 314 has a metal arm 335 extending into the primary coil 332 and adapted to be ultrasonically vibrated by the primary coil 332. The secondary coil 326 is supported by the metal arm 335 and positioned to be inductively coupled to the primary coil 332. The light source 322 and 324 are connected by an electrical conductor to the secondary coil 326. Light from light sources 322 and 324 is focused by lenses 350L and 352L into light guides 350 and 352 respectively. The light passes through light guides 350 and 352 and provides light adjacent to the tip 314.

Alternatively a light guide which is curved in a plane perpendicular to its central axis, such as a cylindrical light guide, is substituted for light guides 350 and 352. Additional light sources connected by an electrical conductor to the secondary coil 326 are preferably evenly distributed around the circular end of the cylindrical light guide With more particular reference to FIGS. 24 through 26 is seen an ultrasonic handpiece system 410, comprising: handpiece housing 412, scaling tip 414, insert 416, light sources 422 and 424, a primary coil 432 and a secondary coil 426. Secondary coil 426 is connected to light sources 422 and 424 by electrical conductors 418 and 428. Primary coil 432 is connected to ultrasonic drive circuit 436 by electrical conductor 434. Ultrasonic drive circuit 436 is connected by electrical conductor 338 to alternating current drive circuit 440. Alternating current drive circuit 440 is connected to a power source, such as a 110 volt alternating current power source. The scaling tip 414 has a metal arm 435 extending into the primary coil 432 and adapted to be ultrasonically vibrated by the primary coil 432. The secondary coil 426 is supported by the metal arm 435 and positioned to be inductively coupled to the primary coil 432. The light source 422 and 424 are connected by an electrical conductor to the secondary coil 426. The light sources 422 and 424 provide light adjacent to the tip 414.

The invention provides a lighted ultrasonic scalar insert for use in the dental industry. A preferred embodiment of the invention provides an insert has a light source. An ultrasonic dental insert is comprised of a magnetostrictive motor, which converts electrical power into mechanical motion. The magnetostrictive actuator converts electrical energy to high frequency mechanical energy using the magnetic field induced by an electric current in a wound wire solenoid, or coil. In layman terms, it converts electrical energy input into a high frequency mechanical displacement output. The mechanical energy produced is transmitted through a connecting body to the scalar tip. This scalar tip motion is used to remove calculus or stains in dental procedures. The light illuminate the tip and working area. This lighted portion of the ultrasonic scalar insert utilizes either an external power source or external light source to assist in illuminating the tip of the ultrasonic insert. FIGS. 7 through 26 show lighted ultrasonic scalar inserts. These ultrasonic inserts, when installed in the ultrasonic dental hand piece, provide light to illuminate the dental scaling procedure area. The light source can either is an incandescent bulb, halogen bulb, or light emitting diode (LED). FIGS. 21 through 23 show a device having an optical light pipe or bundle to transmit the light. The illumination for the fiber optic light pipe originates in the handpiece transmitting light from either an incandescent bulb, halogen bulb, or light emitting diode (LED). An internal water passage is provided for a lavage at the tip.

Transmitting light onto the tip eliminates the need for other supplemental light sources during a dental scaling procedure. The light source utilizes the power available in the coil of the handpiece. An additional inductive coil utilizes the available power in the coil magnetic field. The device operates in the ultrasonic frequency range, frequencies greater than 18 K Hertz, but it not is specifically limited to this frequency range. The significance of operating in the ultrasonic frequency range is the scaling performance. The higher frequencies are considered optimal for scale removal because it is efficient and provides higher patient comfort in comparison to the relatively lower frequency units.

The light transmitted from the insert assists in illuminating the dental scaling procedure site. The ultrasonic insert is rotate in the handpiece allowing easier tip manipulation. The location where light is introduced eliminates the possibility of hand or finger obstructions. Utilizing power from the coil is preferred as this does not require additional wiring in the handpiece or cable which would lends to hand fatigue during scaling. The entire device is autoclave sterilizable.

Preferably metal arm 31, 135, 235, 335 and 435 is each a stack of metal plates connected by an electrical conductor. For example the electrical conductor is a metal weld holding the stack of metal plates together.

A preferred embodiment of the invention provides an ultrasonic handpiece system comprising a scaling tip, a light guide, at least one light source, a primary coil and a secondary coil. The scaling tip has a metal arm extending into the primary coil and adapted to be ultrasonically vibrated by the primary coil. The secondary coil is positioned to be inductively coupled to the primary coil. The light source is connected by at least one electrical conductor to the secondary coil. The light source is positioned to transmit light into the light guide. Preferably, the light from the light source is transmitted through the light guide onto the tip. Preferably, the light from the light source is transmitted through the light guide and onto a tooth positioned adjacent to the tip. Preferably, the metal arm comprises a plurality of metal plates.

Preferably, the ultrasonic handpiece system includes at least two pairs of electrical contacts, one member of each the pair of electrical contacts is connected by at least one electrical conductor to the secondary coil, and the other member of each the pair of electrical contacts is connected by at least one electrical conductor to the light source. Preferably, the ultrasonic handpiece system includes an ultrasonic drive circuit and an alternating current drive circuit, the ultrasonic drive circuit is connected by at least one electrical conductor to the alternating current drive circuit, and the ultrasonic drive circuit is connected by at least one electrical conductor to the primary coil. Preferably, the ultrasonic handpiece system includes at least one light guide, the light source is positioned to transmit light into the light guide.

Preferably, the ultrasonic handpiece system includes an ultrasonic drive circuit and an alternating current drive circuit, the ultrasonic drive circuit is connected by at least one electrical conductor to the alternating current drive circuit, and the ultrasonic drive circuit is connected by at least one electrical conductor to the primary coil. Preferably, the light source comprises an incandescent bulb, an halogen bulb, or a light emitting diode (LED).

A preferred embodiment of the invention provides a dental method, comprising: providing a scaling tip having an arm extending into a primary coil enclosed by a housing and sliding a secondary coil over the housing. Preferably at least one light source electrically connected to the secondary coil. Preferably the secondary coil is positioned to be inductively coupled to the primary coil, and the light source is positioned to transmit light onto the scaling tip. Light is emitted from the light source onto a tooth positioned adjacent to the scaling tip. Then the tooth is scaled.

A preferred embodiment of the invention provides a lighting device, consisting essentially of: a coil, a control circuit and a light source, the coil being connected to the control circuit and to the light source.

A preferred embodiment of the invention provides an ultrasonic scaler handpiece system, comprising: a scaler handpiece housing supporting a scaling tip, enclosing a primary coil, and a light source housing supporting a secondary coil and a light source, the scaler handpiece housing supporting the light source housing.

A preferred embodiment of the invention provides a method comprising: sliding a lighting sleeve onto a dental handpiece, the dental handpiece enclosing a primary coil, the lighting sleeve, having a secondary coil, and a light source, the secondary coil being connected to the light source.

A preferred embodiment of the invention provides an ultrasonic handpiece system comprising a scaling tip, a light guide, at least one light source, a primary coil and a secondary coil, wherein the scaling tip has a metal arm extending into the primary coil and adapted to be ultrasonically vibrated by the primary coil, the secondary coil is positioned to be inductively coupled to the primary coil, the light source is connected by at least one electrical conductor to the secondary coil, the light source is positioned to transmit light into the light guide.

A preferred embodiment of the invention provides an ultrasonic handpiece system, comprising: a scaling tip, at least one light source, a primary coil and a secondary coil, wherein the scaling tip has a metal arm extending into the primary coil and adapted to be ultrasonically vibrated by the primary coil, the secondary coil is supported by the metal arm and positioned to be inductively coupled to the primary coil, and the light source is connected by at least one electrical conductor to the secondary coil, the light source is positioned to transmit light adjacent to the tip.

A preferred embodiment of the invention provides an ultrasonic handpiece system, comprising: a scaling tip, at least one light source, a primary coil and a secondary coil, and a tertiary coil, wherein the scaling tip has a metal arm extending into the primary coil and adapted to be ultrasonically vibrated by the primary coil, the secondary coil is supported by the metal arm and positioned to be inductively coupled to the primary coil, the tertiary coil is positioned to be inductively coupled to the secondary coil, the light source is connected by at least one electrical conductor to the tertiary coil, and the light source is positioned to transmit light adjacent to the tip.

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A dental method, comprising:
   providing a scaling tip having an arm extending into a primary coil enclosed by a housing and
   sliding a secondary coil over the housing.

2. The method of claim 1 further comprising at least one light source electrically connected to said secondary coil.

3. The method of claim 2 further comprising emitting light from said light source onto a tooth positioned adjacent to said scaling tip.

4. The method of claim 3 further comprising scaling said tooth with said tip.

5. The method of claim 1 wherein said secondary coil is positioned to be inductively coupled to said primary coil, and said light source is positioned to transmit light onto said scaling tip.

6. The method of claim 1 further comprising two light emitting diodes electrically connected to said secondary coil.

7. The method of claim 1 further comprising at least one diode electrically connected to said secondary coil.

8. An ultrasonic scaler handpiece system, comprising:
   a scaler handpiece housing supporting a scaling tip, enclosing a primary coil, and
   a light source housing supporting a secondary coil and a light source,
      said scaler handpiece housing supporting said light source housing.

9. A method comprising:
   sliding a lighting sleeve onto a dental handpiece,
      said dental handpiece enclosing a primary coil,
      said lighting sleeve, having a secondary coil, and
   a light source,
      said secondary coil being connected to said light source.

10. The method of claim 9 wherein said dental handpiece has a rigid housing and said lighting sleeve has a flexible housing.

11. An ultrasonic handpiece system comprising a scaling tip, a light guide, at least one light source, a primary coil and a secondary coil,
   the scaling tip having a metal arm extending into the primary coil and adapted to be ultrasonically vibrated by said primary coil,
   said secondary coil being positioned to be inductively coupled to said primary coil,
   said light source being connected by at least one electrical conductor to said secondary coil, and
   said light source being positioned to transmit light into said light guide.

12. The ultrasonic handpiece system of claim 11 wherein light from said light source is transmitted through said light guide onto said tip.

13. The ultrasonic handpiece system of claim 11 wherein light from said light source is transmitted through said light guide and onto a tooth positioned adjacent to said tip.

14. The ultrasonic handpiece system of claim 11 wherein said metal arm comprises a plurality of metal plates.

15. An ultrasonic handpiece system, comprising:
   a scaling tip, at least one light source, a primary coil and a secondary coil,
      said scaling tip having a metal arm extending into said primary coil and adapted to be ultrasonically vibrated by said primary coil,
      said secondary coil being supported by said metal arm and positioned to be inductively coupled to said primary coil,
      said light source being connected by at least one electrical conductor to said secondary coil, and
      said light source being positioned to transmit light adjacent to said tip.

16. The ultrasonic handpiece system of claim 15 wherein light from said light source is transmitted onto a tooth positioned adjacent to said tip.

17. The ultrasonic handpiece system of claim 15 further comprising at least two pairs of electrical contacts, one member of each said pair of electrical contacts being connected by at least one electrical conductor to said secondary coil, and the other member of each said pair of electrical contacts being connected by at least one electrical conductor to said light source.

18. The ultrasonic handpiece system of claim 15 further comprising an ultrasonic drive circuit and an alternating current drive circuit, said ultrasonic drive circuit being connected by at least one electrical conductor to said alternating current drive circuit, and said ultrasonic drive circuit being connected by at least one electrical conductor to said primary coil.

19. The ultrasonic handpiece system of claim 15 further comprising at least one light guide, said light source being positioned to transmit light into said light guide.

20. An ultrasonic handpiece system, comprising:
   a scaling tip, at least one light source, a primary coil and a secondary coil, and a tertiary coil,
      said scaling tip having a metal arm extending into said primary coil and adapted to be ultrasonically vibrated by said primary coil,
      said secondary coil being supported by said metal arm and positioned to be inductively coupled to said primary coil,
      and said tertiary coil being positioned to be inductively coupled to said secondary coil,
      said light source being connected by at least one electrical conductor to said tertiary coil, and
      said light source being positioned to transmit light adjacent to said tip.

21. The ultrasonic handpiece system of claim 20 further comprising an ultrasonic drive circuit and an alternating current drive circuit, said ultrasonic drive circuit being connected by at least one electrical conductor to said alternating current drive circuit, and said ultrasonic drive circuit being connected by at least one electrical conductor to said primary coil.

22. The ultrasonic handpiece system of claim 20 wherein said light source comprises an incandescent bulb, an halogen bulb, or a light emitting diode (LED).

* * * * *